US009165358B2

(12) United States Patent
Imai

(10) Patent No.: US 9,165,358 B2
(45) Date of Patent: Oct. 20, 2015

(54) IMAGE PROCESSING APPARATUS, IMAGE PROCESSING METHOD AND IMAGE PROCESSING PROGRAM

(71) Applicant: FUJIFILM Corporation, Minato-Ku, Tokyo (JP)

(72) Inventor: Yoshiro Imai, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/035,324

(22) Filed: Sep. 24, 2013

(65) Prior Publication Data

US 2014/0023257 A1 Jan. 23, 2014

Related U.S. Application Data

(63) Continuation of application No. PCT/JP2012/002011, filed on Mar. 23, 2012.

(30) Foreign Application Priority Data

Mar. 24, 2011 (JP) .................................. 2011-065509

(51) Int. Cl.
G06T 7/00 (2006.01)
A61B 6/00 (2006.01)
G06T 5/00 (2006.01)
G06T 5/10 (2006.01)

(52) U.S. Cl.
CPC ............. G06T 7/0012 (2013.01); A61B 6/4291 (2013.01); A61B 6/5252 (2013.01); A61B 6/5258 (2013.01); G06T 5/002 (2013.01); G06T 5/10 (2013.01); A61B 6/4216 (2013.01); G06T 2207/10116 (2013.01); G06T 2207/30004 (2013.01)

(58) Field of Classification Search
None
See application file for complete search history.

(56) References Cited

U.S. PATENT DOCUMENTS

| 5,187,369 A | 2/1993 | Kingsley et al. |
| 5,661,818 A | 8/1997 | Gaborski et al. |
| 6,269,176 B1* | 7/2001 | Barski et al. ................. 382/128 |
| 8,097,839 B2 | 1/2012 | Yamakita |

(Continued)

FOREIGN PATENT DOCUMENTS

| JP | 59-211263 A | 11/1984 |
| JP | 1-216290 A | 8/1989 |

(Continued)

OTHER PUBLICATIONS

Communication dated Jun. 3, 2014, issued by the Japan Patent Office in corresponding Japanese Application No. 2011-065509.

(Continued)

Primary Examiner — Bhavesh Mehta
Assistant Examiner — Raphael Schwartz
(74) Attorney, Agent, or Firm — Sughrue Mion, PLLC

(57) ABSTRACT

A subject component removed signal is obtained from an image signal representing an image by performing, with respect to a first direction and/or a second direction that is different from the first direction, one-dimensional filtering processing using a subject component removal filter that removes a low frequency component including a subject component of the image to roughly remove the subject component. Further, frequency components corresponding to the periodic pattern in the subject component removed signal are detected with respect to both of the first direction and the second direction.

13 Claims, 6 Drawing Sheets

(56) References Cited

U.S. PATENT DOCUMENTS

2003/0016854 A1  1/2003  Inoue et al.
2007/0019847 A1  1/2007  Inoue et al.
2009/0214130 A1* 8/2009  Yamakita .................... 382/260

FOREIGN PATENT DOCUMENTS

| JP | 2-164067 A    | 6/1990  |
|----|---------------|---------|
| JP | 2-263279 A    | 10/1990 |
| JP | 2002-330344 A | 11/2002 |
| JP | 2003-233818 A | 8/2003  |
| JP | 2004-261514 A | 9/2004  |
| JP | 2009-201569 A | 9/2009  |

OTHER PUBLICATIONS

Yujiro Naruse, et al., "Metal/Amorphous Silicon Multilayer Radiation Detectors", IEEE Transactions on Nuclear Science, Apr. 1989, pp. 1347-1352, vol. 36, No. 2.

L.E. Antonuk, et al., "Signal, noise, and readout considerations in the development of amorphous silicon photodiode arrays for radiotherapy and diagnostic x-ray imaging", SPIE, 1991, pp. 108-119, vol. 1443.

S. Qureshi, et al., "Material Parameters in Thick Hydrogenated Amorphous Silicon Radiation Detectors", Journal of Non-Crystalline Solids, 1989, pp. 1347-1352, vol. 36, No. 2.

Communication dated May 13, 2015, issued by the European Patent Office in counterpart Application No. 12761048.3.

* cited by examiner

IMAGE PROCESSING APPARATUS, IMAGE PROCESSING METHOD AND IMAGE PROCESSING PROGRAM

BACKGROUND OF THE INVENTION

1. Field of the Invention

The present invention relates to an image processing apparatus, method and program that suppresses a spatial frequency component corresponding a periodic pattern in an image signal. In particular, the present invention relates to an image processing apparatus, method and program that suppresses a periodic pattern in a radiographic image caused by a grid used in radiography.

2. Description of the Related Art

Conventionally, storable phosphors (photostimulable phosphors) have been used. When a storable phosphor is irradiated with radiation (X-rays, α-rays, β-rays, γ-rays, an electron beam, ultraviolet rays or the like), apart of radiation energy is stored in the storable phosphor. After then, when excitation light, such as visible light and a laser beam, is output to the storable phosphor, the storable phosphor emits photoluminescence corresponding to the radiation energy stored therein. For example, a radiographic image readout apparatus using the storable phosphor is widely used in CR (Computed Radiography). A storable phosphor sheet, in which the storable phosphor is deposited on a substrate, is irradiated with radiation that has passed through a subject, such as a human body, and radiographic information is temporarily stored and recorded on the storable phosphor sheet. Excitation light, such as a laser beam, is output to the storable phosphor sheet to induce photoluminescence. Further, photoelectric conversion is performed on the photoluminescence to obtain an image signal.

Here, when a radiographic image of a subject is imaged and recorded on the storable phosphor sheet or the like, imaging is performed by placing a grid between the subject and the sheet in some cases so that radiation scattered by the subject does not irradiate the sheet. In the grid, lead or the like, which does not pass radiation therethrough, and aluminum, wood or the like, which tends to pass radiation therethrough, are alternately arranged at a narrow pitch of 4 line/mm. When radiography is performed by using the grid, radiation scattered by the subject does not tend to irradiate the sheet. Therefore, it is possible to improve the contrast of the radiographic image of the subject. However, when the size of the image including this grid image is enlarged or reduced, aliasing due to folding occurs depending on the magnification or reduction ratio. Further, when aliasing overlaps with the spatial frequency of the grid image or the like, a narrow stripe pattern (moire) is generated, and observation of a regenerated image becomes difficult. Therefore, there is a demand for a method for detecting the direction of a periodic pattern, such as a grid image and a moire, and a spatial frequency component corresponding to the periodic pattern, and removing the spatial frequency component corresponding to the periodic pattern in the detected direction.

U.S. Pat. No. 5,661,818 (Patent Document 1) discloses, as a method for removing such a periodic pattern from an image, a method in which filtering is performed in two directions of a vertical direction and a horizontal direction of the image by a high-pass filter, and variance values of the result of filtering are calculated with respect to the two directions of the vertical direction and the horizontal direction, and a direction in which a grid image is present is detected based on the ratio of the variance values.

Further, Japanese Unexamined Patent Publication No. 2003-233818 (Patent Document 2) discloses a method in which peaks of frequency patterns are detected with respect to a horizontal direction and a vertical direction. When the peaks of the frequency patterns have been detected in both of the horizontal direction and the vertical direction, a direction in which the magnitude of the peak is greater than a predetermined threshold is judged as the direction of a grid image.

Further, U.S. Pat. No. 8,097,839 (Patent Document 3) discloses an image processing method. In the method, two-dimensional Fourier transformation is performed on image data to detect a spatial frequency component corresponding to a periodic pattern. Further, filtering is performed by using a filter that removes only the detected spatial frequency component.

SUMMARY OF THE INVENTION

Here, such a periodic pattern is not always parallel to a horizontal direction or a vertical direction of an image, but inclined from the horizontal direction or the vertical direction of the image in some cases. However, the methods disclosed in Patent Document 1 and 2 detect presence of a periodic pattern either in the horizontal direction or in the vertical direction. Therefore, it is impossible to accurately detect the inclination of the periodic pattern.

In the method disclosed in Patent Document 3, the load of calculation is high, because a spatial frequency component corresponding a periodic pattern is detected by two-dimensional Fourier transformation. Therefore, there is a demand for a method for accurately detecting the inclination of the periodic pattern with a lower calculation load.

In view of the foregoing circumstances, it is an object of the present invention to provide an image processing apparatus, an image processing method and an image processing program that can detect the inclination of a periodic pattern with a relatively low calculation load.

An image processing apparatus of the present invention is an image processing apparatus that identifies the inclination of a periodic pattern included in an image based on frequency components corresponding to the periodic pattern, and the frequency components having been detected with respect to a plurality of directions, the apparatus comprising:

a subject component removal means that obtains a subject component removed signal from an image signal representing the image by performing, with respect to a first direction and/or a second direction that is different from the first direction, one-dimensional filtering processing using a subject component removal filter that removes a low frequency component including a subject component of the image to roughly remove the subject component; and a periodic pattern detection means that detects, with respect to both of the first direction and the second direction, the frequency components corresponding to the periodic pattern in the subject component removed signal.

An image processing method of the present invention is an image processing method that identifies the inclination of a periodic pattern included in an image based on frequency components corresponding to the periodic pattern, and the frequency components having been detected with respect to a plurality of directions, the method comprising the steps of:

obtaining a subject component removed signal from an image signal representing the image by performing, with respect to a first direction and/or a second direction that is different from the first direction, one-dimensional filtering processing using a subject component removal filter that removes a low frequency component including a subject component of the image to roughly remove the subject component; and detecting, with respect to both of the first direction and the second direction, the frequency components corresponding to the periodic pattern in the subject component removed signal.

An image processing program of the present invention is an image processing program that identifies the inclination of a periodic pattern included in an image based on frequency components corresponding to the periodic pattern, and the frequency components having been detected with respect to a plurality of directions, the program causing a computer to function as:

a subject component removal means that obtains a subject component removed signal from an image signal representing the image by performing, with respect to a first direction and/or a second direction that is different from the first direction, one-dimensional filtering processing using a subject component removal filter that removes a low frequency component including a subject component of the image to roughly remove the subject component; and a periodic pattern detection means that detects, with respect to both of the first direction and the second direction, the frequency components corresponding to the periodic pattern in the subject component removed signal.

The term "periodic pattern" means a noise having a periodic pattern included in an original image. For example, the periodic pattern means a grid image, moire or the like included in an original image when a radiographic image is imaged on a storable phosphor sheet by using the grid.

Here, the phrase "a second direction that is different from the first direction" may mean any direction as long as the second direction is at a certain angle or greater to the first direction in such a manner that the inclination of the periodic pattern is identifiable. It is desirable that the second direction is closer to a direction orthogonal to the first direction.

Further, the subject component removal means may remove a low frequency component including a subject component only in a predetermined direction, such as a horizontal direction or a vertical direction. Alternatively, the subject component removal means may remove low frequency components in plural directions.

Further, the range of a low frequency component removed by the subject component removal filter may be set at an arbitrary range as long as a subject component is included. Further, the subject component removal filter may be a high-pass filter that removes, with respect to at least one of the first direction and the second direction, a lower frequency component or components than the detected frequency component or components corresponding to the periodic pattern from the image signal. Alternatively, the subject component removal filter may be a band-pass filter that extracts, with respect to at least one of the first direction and the second direction, a spatial frequency component or components including the detected frequency component or components corresponding to the periodic pattern from the image signal.

Further, the subject component removal filter may remove, with respect to one of the first direction and the second direction that has the clearer peak of a frequency spectrum of the detected frequency component corresponding to the periodic pattern, a lower spatial frequency component than the frequency component corresponding to the periodic pattern, and which has been detected with respect to the one of the first direction and the second direction, from the image signal. Further, the periodic pattern detection means may detect, with respect to at least the other one of the first direction and the second direction, the frequency component corresponding to the periodic pattern in the subject component removed signal.

Here, the expression "has the clearer peak of a frequency spectrum" means that any judgment method may be used as long as the feature that the frequency component corresponds to a periodic pattern is more clearly recognizable. For example, when a difference in frequency spectra between a peak of a frequency spectrum detected for each of plural directions and a frequency spectrum in the vicinity of the peak is the largest, the peak may be judged as the clearer peak.

It is desirable that the image processing apparatus of the present invention further includes a suppression means that suppresses the frequency components corresponding to the periodic pattern in the image by performing, with respect to both of the first direction and the second direction, one-dimensional filtering processing for suppressing the frequency components corresponding to the periodic pattern, and which have been detected with respect to both of the first direction and the second direction, on the image.

It is desirable that the image processing apparatus of the present invention further includes a warning means that warns when the frequency components corresponding to the periodic pattern have been detected with respect to both of the first direction and the second direction.

In that case, a warning may be issued in any method as long as the warning is identifiable by a user. For example, the warning may be issued by sound or by a visual means.

According to the image processing apparatus, image processing method and image processing program of the present invention, a subject component removed signal is obtained from an image signal by performing, with respect to a first direction and/or a second direction that is different from the first direction, one-dimensional filtering processing using a subject component removal filter that removes a low frequency component including a subject component of an image to roughly remove the subject component. Further, the frequency components corresponding to the periodic pattern are detected in the subject component removed signal with respect to both of the first direction and the second direction. Therefore, rough removal of the low frequency components can reduce a risk that detection of a peak of a frequency spectrum of a periodic pattern becomes difficult because of a subject component included in a low frequency band. Hence, it is possible to appropriately detect a frequency component corresponding a periodic pattern based on the subject component removed signal. Further, subject component removal processing and periodic pattern detection processing are performed by one-dimensional filtering processing. Therefore, it is possible to accurately detect the frequency components corresponding to the periodic pattern in an appropriate manner with a relatively low calculation load. Consequently, it is possible to appropriately remove a periodic pattern, such as moire, based on the detected inclination of the image. Hence, it is possible to obtain a high quality image appropriate for diagnosis based on the image.

DESCRIPTION OF THE PREFERRED EMBODIMENTS

Hereinafter, embodiments of the present invention will be described with reference to drawings. In the following embodiments, a case in which a periodic pattern suppression processing apparatus according to the present invention is used in a radiographic image readout apparatus will be described. Alternatively, the periodic pattern suppression processing apparatus may be used in an image processing apparatus or the like for suppressing a periodic pattern included in a photographic image that was obtained in ordinary photography using a digital camera or the like when photography was performed through a window screen, a blind or the like. Here, the radiographic image readout apparatus reads out, as a digital image signal, a radiographic image of a human body recorded on a storable phosphor sheet by scanning the radiographic image with a laser beam.

Figure 1:
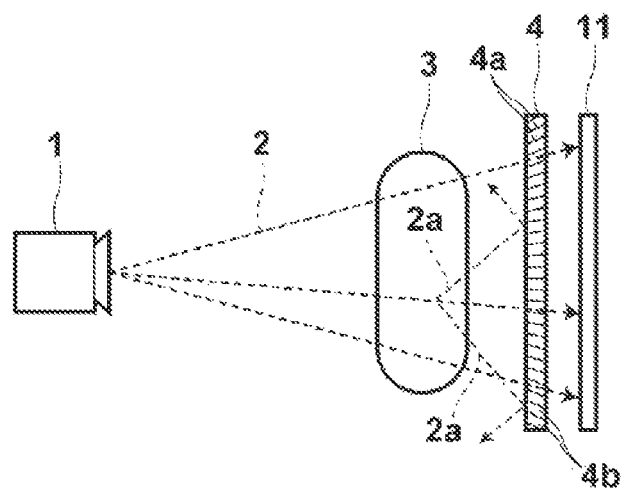
FIG. 1 is a schematic diagram illustrating a radiography apparatus.

FIG. 1 is a schematic diagram illustrating a radiography apparatus. Radiation 2 is output from a radiation source 1, and passes through a subject 3, and reaches a static grid (hereinafter, simply referred to as "grid") 4. In the grid 4, lead 4a, which absorbs the radiation 2, and aluminum 4b, which passes the radiation 2, are alternately arranged, for example, at a pitch of about 4 line/mm. Further, the lead 4a is set in such a manner that the inclination of the lead 4a is slightly different depending on its position so that the radiation 2 passes through the aluminum 4b, and enters a storable phosphor sheet 11.

Figure 2:
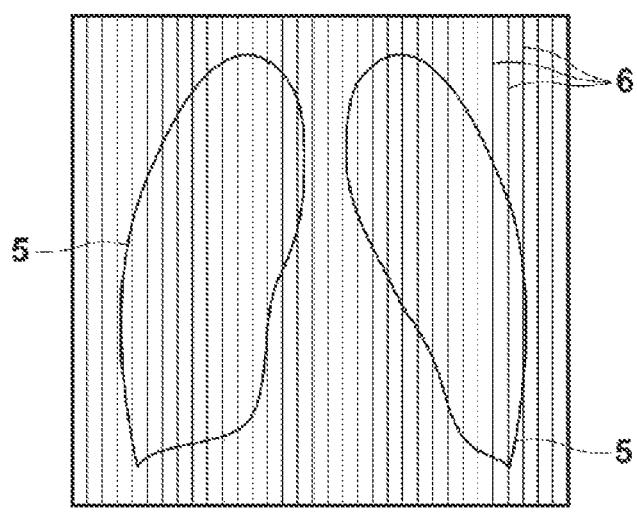
FIG. 2 is a diagram illustrating a radiographic image obtained by imaging with a grid.

Therefore, the radiation 2 that has passed through the subject 3 is absorbed by the lead 4a, and does not reach the storable phosphor sheet 11. However, the radiation 2 passes through the aluminum 4b, and reaches the storable phosphor sheet 11. A grid image of a stripe pattern of 4 line/mm is recorded on the storable phosphor sheet 11 together with a subject image. Meanwhile, scattered radiation 2a, which is scattered in the subject 3, is absorbed by the lead 4a, which is set in such a manner to be inclined depending on its position, or reflected by the surface of the grid 4. Therefore, the scattered radiation 2a does not reach the storable phosphor sheet 11. Hence, the storable phosphor sheet 11 can record a sharp radiographic image with a little amount of scattered radiation 2a irradiating the storable phosphor sheet 11. FIG. 2 is a diagram illustrating an example of a radiographic image of a subject image 5 and a grid image 6. The radiographic image is stored and recorded on the storable phosphor sheet 11 when radiography is performed by using the radiography apparatus illustrated in FIG. 1.

Figure 3:
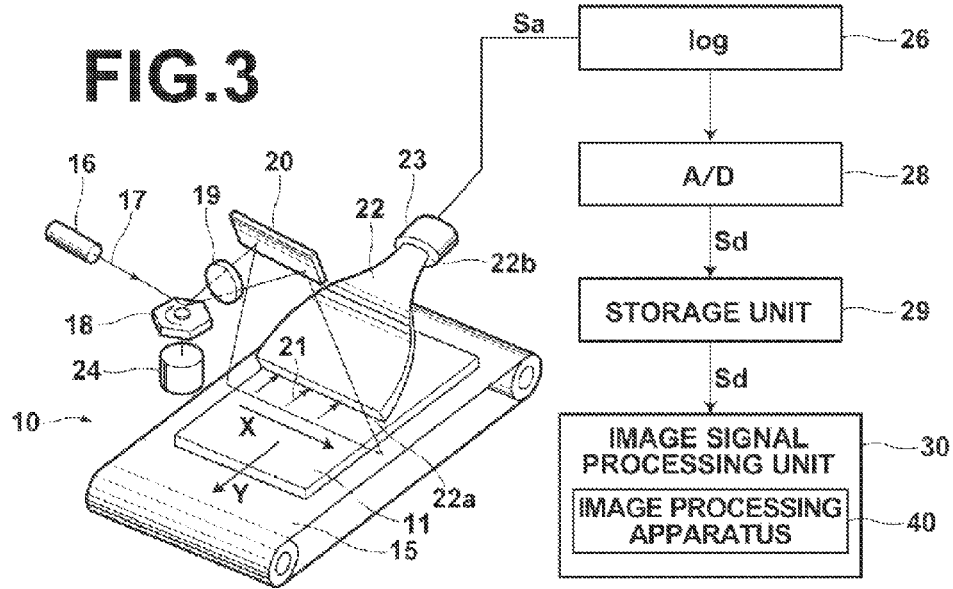
FIG. 3 is a perspective view illustrating an example of a radiographic image readout apparatus.

FIG. 3 is a diagram illustrating a perspective view and a functional block diagram of a radiographic image readout apparatus in combination. The storable phosphor sheet 11 is set at a predetermined position of a readout unit 10, and conveyed by a sheet conveyance means 15, such as an endless belt, which is driven by a drive means (not illustrated). The storable phosphor sheet 11 is conveyed (sub-scanned) in the direction of arrow Y, for example, at a scan pitch of 10 line/mm. Meanwhile, a light beam 17 is output from a laser beam source 16, and reflected by a rotary polyhedral mirror 18 toward a condensing lens 19, such as an fθ lens. The rotary polyhedral mirror 18 is driven by a motor 24, and rotates at high speed in the direction of an arrow. After the light beam 17 passes through the condensing lens 19, the light beam 17 is reflected by a mirror 20 toward the storable phosphor sheet 11. The storable phosphor sheet 11 is main-scanned by the light beam 17 in the direction of arrow X, which is at a substantially right angle to the sub-scan direction (the direction of arrow Y).

When the storable phosphor sheet 11 is illuminated with the light beam 17, stimulated emission light 21 in an amount corresponding to radiographic image information stored and recorded at an illuminated position of the storable phosphor sheet 11 is emitted from the position. The stimulated emission light 21 enters a light guide 22 from an incident end surface 22a of the light guide 22, and repeats total reflection in the light guide 22, and is output from an output end surface 22b of the light guide 22. The output stimulated emission light 21 is received by a photomultiplyer 23, and converted into analog image signal Sa by photoelectric conversion.

Figure 4:
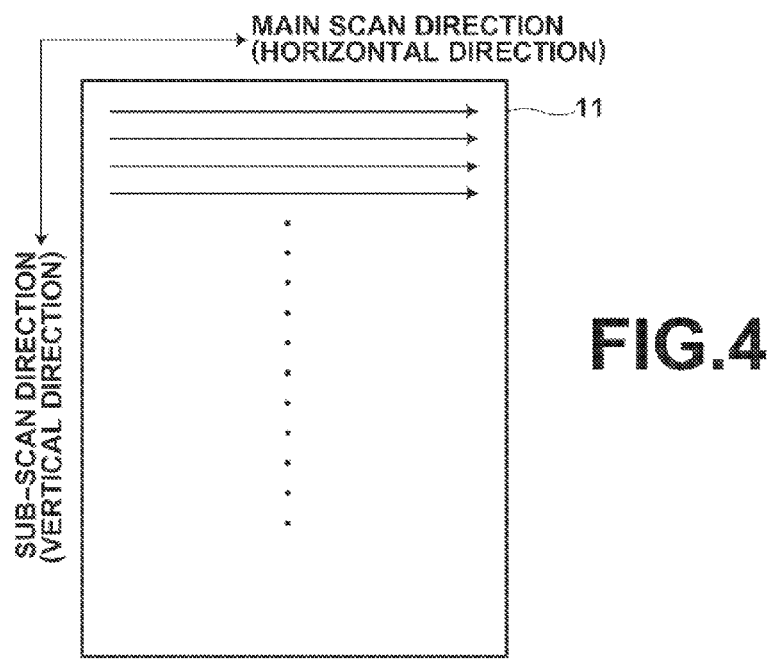
FIG. 4 is a diagram illustrating a relationship between scan directions and an image to be read out.

After the analog image signal Sa is logarithmically amplified by a log amplifier 26, the analog image signal Sa is sampled with a sampling interval corresponding to a spatial frequency of fs=10 cycle/mm and digitized by an A/D converter 28, and digital image signal Sd (hereinafter, simply referred to as "image signal Sd") is output. The image signal Sd represents radiographic image information obtained by two-dimensionally scanning the storable phosphor sheet 11. As illustrated in FIG. 4, the radiographic image information is obtained by moving the storable phosphor sheet 11 in a sub-scan direction (vertical direction) while the storable phosphor sheet 11 is scanned with the light beam 17 in a main scan direction (horizontal direction). The image signal Sd obtained in this manner includes information about the grid image 6 corresponding to the grid 4 in addition to information about the radiographic image 5 corresponding to the subject 3.

After the image signal Sd is temporarily stored in a storage unit 29, the image signal Sd is input to an image signal processing unit 30. The image signal processing unit 30 includes an image processing apparatus 40 for performing an image processing method in the present invention.

Figure 5A:
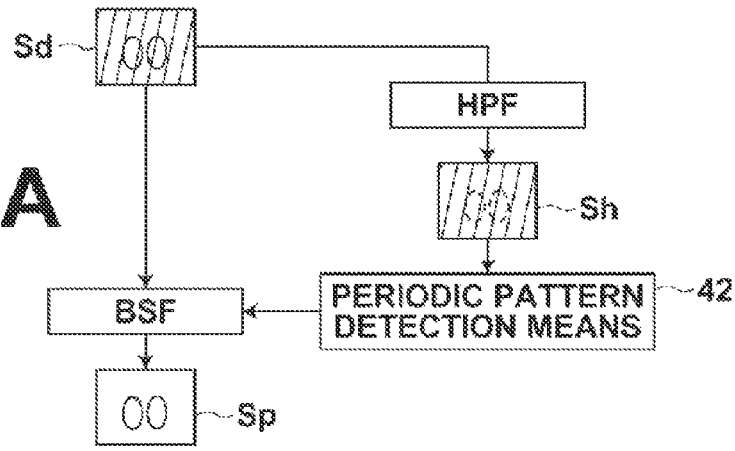
FIG. 5A is a diagram illustrating a flow of processing in an image processing apparatus according to a first embodiment.
Figure 6:
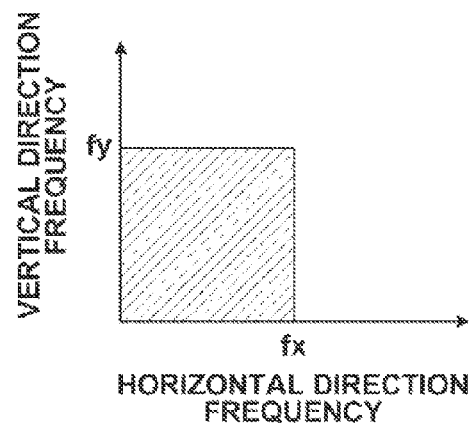
FIG. 6 is a diagram illustrating subject component removal characteristics according to the first embodiment.
Figure 7A:
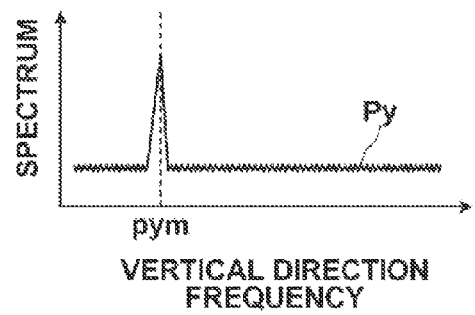
FIG. 7A is a diagram for explaining vertical-direction periodic pattern detection processing according to the first embodiment.
Figure 7B:
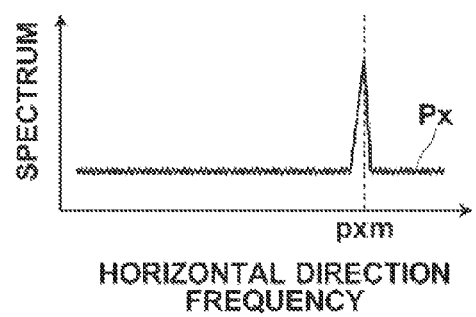
FIG. 7B is a diagram for explaining horizontal-direction periodic pattern detection processing according to the first embodiment.
Figure 7C:
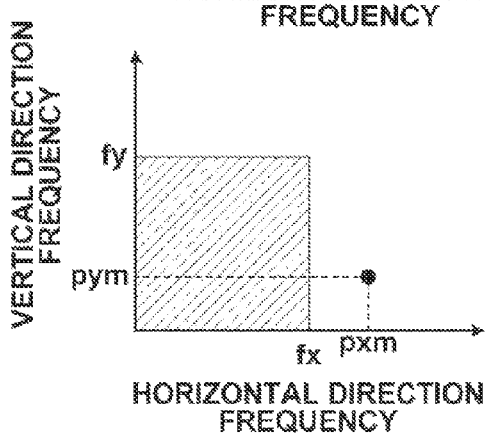
FIG. 7C is a diagram illustrating a frequency component corresponding to a periodic pattern, and the frequency component being detected in the first embodiment.

FIG. 5A is a diagram illustrating a flow of processing in the image processing apparatus 40 according to the first embodiment. FIG. 6 is a diagram illustrating subject component removal characteristics according to the first embodiment. FIGS. 7A, 7B and 7C are diagrams for explaining periodic pattern detection processing in the embodiment of the present invention. FIGS. 7A and 7B illustrate frequency spectra (vertical direction frequency spectrum Py and horizontal direction frequency spectrum Px) that have been obtained by performing fast Fourier transformation on subject component removed signal Sh, respectively. Further, FIG. 7C illustrates the inclination of a periodic pattern, using detected frequency components pxm and pym. The image processing apparatus 40 according to the embodiment of the present invention will be described with reference to FIG. 5A and FIG. 6 through FIG. 7C.

As illustrated in FIG. 5A, the image processing apparatus 40 according to the embodiment of the present invention includes a subject component removal means 41, a periodic pattern detection means 42 and a suppression means 43. The subject component removal means 41 obtains a subject component removed signal from an image signal representing an image by performing, with respect to a first direction (horizontal direction) and/or a second direction (vertical direction) that is different from the first direction, one-dimensional filtering processing using a subject component removal filter (HPF in FIG. 5A) that removes a low frequency component including a subject component of the image to roughly remove the subject component from the image. The periodic pattern detection means 42 detects, with respect to both of the first direction and the second direction, the frequency components corresponding to the periodic pattern in subject component removed signal Sh. The suppression means 43 suppresses the frequency components corresponding to the periodic pattern in the image by performing, with respect to both of the first direction and the second direction, one-dimensional filtering processing on the image by using band-stop filter BSF that suppresses the frequency components corresponding to the periodic pattern, and the frequency components having been detected with respect to both of the first direction and the second direction.

An image processing program in an embodiment of the present invention and data to which the image processing program refers are stored in the storage unit 29 when the image processing program is installed, and loaded in a memory included in the storage unit 29 when the image processing program is started. The image processing program defines subject component removal processing, periodic pattern detection processing and suppression processing, as processing performed by a central processing unit of the image signal processing unit 30, which constitutes the image processing apparatus 40. The central processing unit executes each of the aforementioned kinds of processing based on the program. Accordingly, the central processing unit of the image signal processing unit 30 functions as the subject component removal means 41, the periodic pattern detection means 42, and the suppression means 43.

FIG. 6 is a diagram illustrating an example of high-pass filter HPF used in subject component removal processing in the embodiment of the present invention. The subject component removal means 41 performs one-dimensional filtering processing by a high-pass filter, as illustrated in FIG. 6. The high-pass filter passes a frequency component higher than or equal to frequency fx in a horizontal direction, and a frequency component higher than or equal to frequency fy in a vertical direction. Accordingly, the subject component removal means 41 obtains subject component removed signal Sh.

The periodic pattern detection means 42 performs, with respect to a horizontal direction and a vertical direction, frequency analysis on the obtained subject component removed signal Sh, as illustrated in FIG. 7A and FIG. 7B. The periodic pattern detection means 42 detects, as frequency components pxm and pym corresponding to the periodic pattern, a peak of a frequency spectrum for each of the directions. Further, the inclination of the periodic pattern is identified based on the detected frequency components pxm and pym.

The suppression means 43 in the embodiment of the present invention determines passband characteristics for suppressing a periodic pattern by using a known method in such a manner that detected frequency components pxm and pym corresponding to the periodic pattern are included. Then, the suppression means 43 creates, based on the determined passband characteristics, one-dimensional band-stop filter BSF for each of a horizontal direction and a vertical direction. Then, the suppression means 43 extracts processed signal Sp, in which the periodic pattern has been suppressed, from image signal Sd by filtering processing using the band-stop filter BSF. Further, an image corresponding to the processed signal Sp is displayed on a display means, such as a monitor (not illustrated), or output to an output means, such as a printer (not illustrated).

According to the embodiment of the present invention, the subject component removal means 41 removes the low frequency component. Therefore, a risk that detection of a peak of a frequency spectrum of a periodic pattern becomes difficult because of a subject component included in a low frequency band is reduced. Hence, it is possible to appropriately detect a frequency component corresponding a periodic pattern based on a subject component removed signal. Further, subject component removal processing and periodic pattern detection processing are performed by one-dimensional filtering processing. Therefore, it is possible to accurately detect a frequency component corresponding to a periodic pattern in an appropriate manner with a relatively low calculation load. Consequently, it is possible to appropriately remove only a periodic pattern, such as moire, based on the detected inclination of the image. Hence, it is possible to obtain a high quality image appropriate for diagnosis based on the image.

Figure 8A:
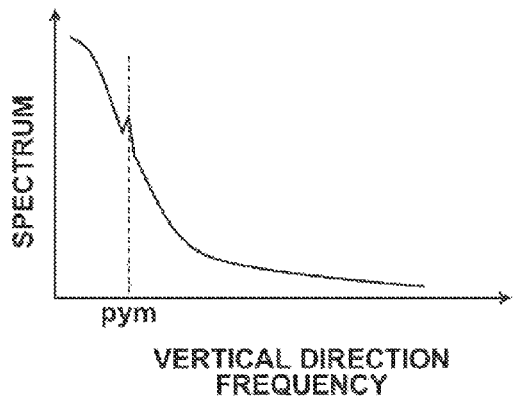
FIG. 8A is a diagram for explaining vertical-direction periodic pattern detection processing according to a method according to the related art.
Figure 8B:
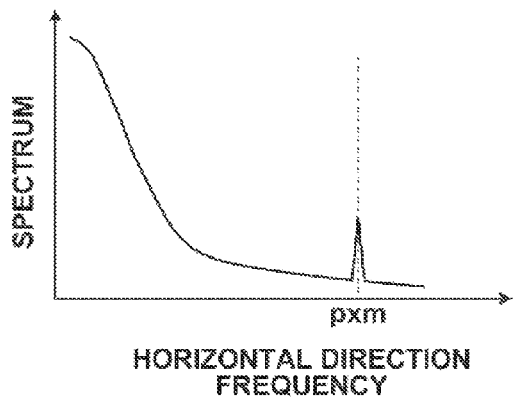
FIG. 8B is a diagram for explaining horizontal-direction periodic pattern detection processing according to a method according to the related art.

FIG. 8A and FIG. 8B are diagrams for explaining a method for detecting a periodic pattern based on frequency spectra. The frequency spectra are calculated by performing frequency analysis on the same image signal Sd as the aforementioned embodiment. FIG. 8A and FIG. 8B illustrate frequency spectra obtained by performing fast Fourier transformation on image signal Sd in a vertical direction and in a horizontal direction, respectively. As illustrated in FIG. 8A, the peak of a frequency spectrum corresponding to the periodic pattern is present in a low frequency band with respect to the vertical direction. However, since many subject components are included in the low frequency band, it is difficult to detect the peak of the frequency spectrum distinguishably from the subject components by using this method. However, according to the embodiment of the present invention, even if the frequency spectrum corresponding to the periodic pattern is present in the low frequency band, as illustrated in FIG. 8A, it is possible to easily detect the peak of the frequency spectrum of the periodic pattern, because periodic pattern detection processing is performed by using a subject component removed signal, in which subject components included in the low frequency band have been removed, as illustrated in FIG. 7A. Further, when the frequency spectrum corresponding to the periodic pattern is present in a high frequency band, as illustrated in 8B, it is possible to more easily detect the peak of the frequency spectrum also by performing periodic pattern detection processing by using a subject component removed signal, in which subject components included in the low frequency band have been removed, as illustrated in FIG. 7B.

In the aforementioned embodiment, the subject component removal means 41 may remove the low frequency component only in a predetermined direction, such as a horizontal direction or a vertical direction. Further, either a high-pass filter or a band-pass filter may be used as long as a low frequency component is removed. Further, the range of the low frequency component to be removed may be set in an arbitrary manner as long as a low frequency component including many subject components is included in the range.

Figure 5B:
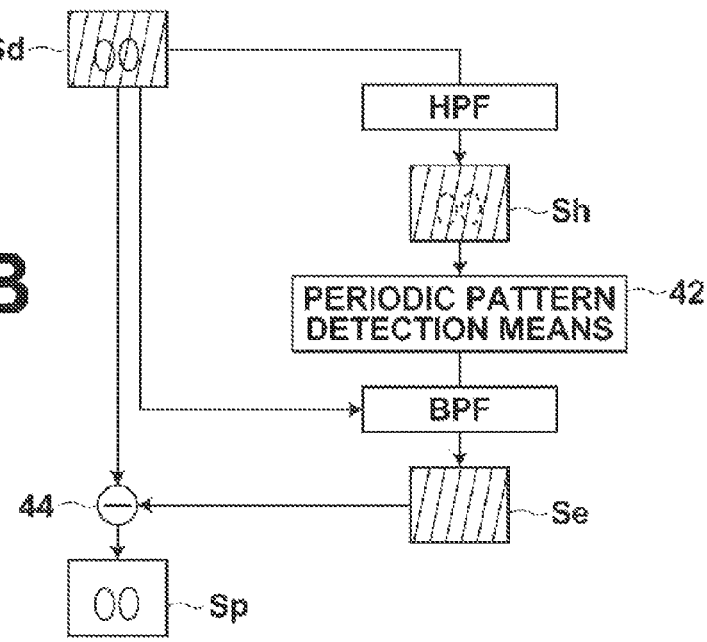
FIG. 5B is a diagram illustrating a flow of processing in an image processing apparatus according to a modified example of the first embodiment.

The suppression means 43 in the aforementioned embodiment may perform any kind of suppression processing as long as processed signal Sp, in which a frequency component corresponding a periodic pattern has been suppressed, is obtainable from image signal Sd. FIG. 5B is a diagram for explaining a modified example of suppression processing in the first embodiment. For example, as illustrated in FIG. 5B, band-pass filter BPF, which passes a band including a detected frequency component corresponding a periodic pattern, may be created, and image signal Se extracted by the band-pass filter BPF may be subtracted from image signal Sd.

Figure 9:
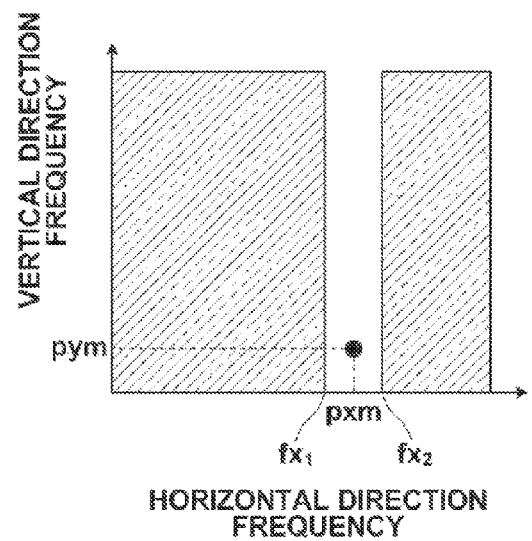
FIG. 9 is a diagram illustrating subject component removal characteristics according to a second embodiment.
Figure 10:
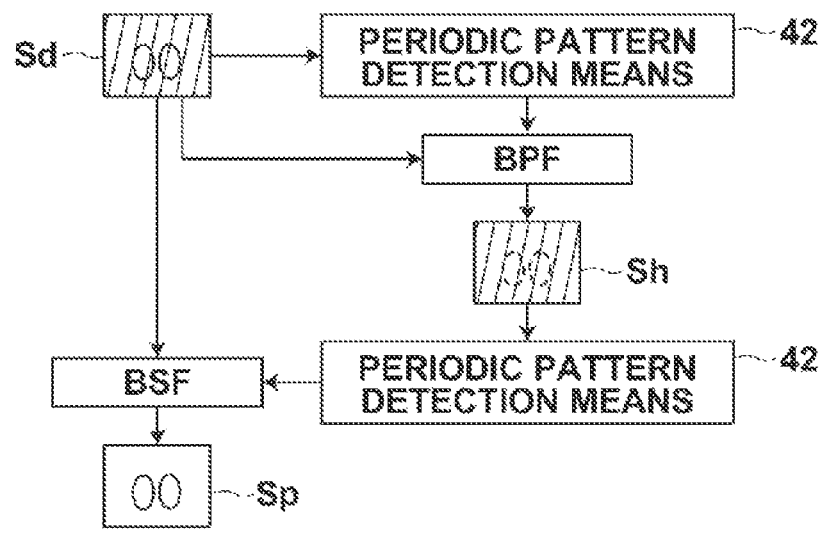
FIG. 10 is a diagram illustrating a flow of processing in an image processing apparatus according to the second embodiment.

Next, a second embodiment will be described. In the second embodiment, the subject component removal means 41 uses, as a subject component removal filter, a band-pass filter that extracts a spatial frequency component or components including a frequency component or components corresponding to a periodic pattern, and the frequency component or components having been detected with respect to at least one of a first direction and a second direction, from an image signal. FIG. 9 is a diagram illustrating the filter characteristics of the subject component removal filter in the second embodiment. FIG. 10 is a diagram for explaining a flow of processing in the image processing apparatus 40 in the second embodiment. Next, a part different from the first embodiment will be mainly described with reference to FIG. 8A through FIG. 10, and an explanation of a part common to the first embodiment and the second embodiment will be omitted.

In the second embodiment, the periodic pattern detection means 42 first performs frequency analysis with respect to a horizontal direction and a vertical direction, and detects peaks of frequency spectra in the horizontal direction and in the vertical direction in image signal Sd. The peaks of the frequency spectra are candidates of spatial frequencies corresponding to the periodic pattern.

Specifically, as illustrated in FIG. 8A and FIG. 8B, the periodic pattern detection means 42 calculates frequency spectra with respect to the vertical direction and the horizontal direction. Further, the periodic pattern detection means 42 detects the peak of the frequency spectrum in each of the horizontal direction and the vertical direction, as a frequency spectrum that has a largest difference from a frequency spectrum in frequencies in the vicinity thereof. Here, it is assumed that a peak is detected at peak frequency pxm in the horizontal direction, as illustrated in FIG. 8B, and that a peak is detected at peak frequency pym in the vertical direction, as illustrated in FIG. 8A.

In the second embodiment, the subject component removal means 41 uses a subject component removal filter that removes, with respect to one of a first direction (horizontal direction) and a second direction (vertical direction) that has the clearer peak of a frequency spectrum of a frequency component corresponding to a periodic pattern, a lower spatial frequency component than the frequency component corresponding to the periodic pattern, and which has been detected with respect to the one of the first direction and the second direction, from image signal Sd.

Specifically, the subject component removal means 41 judges that a probability that peak frequency pxm is a frequency component corresponding to a periodic pattern is high. With respect to peak frequency pxm in the horizontal direction and the peak frequency pxm in the vertical direction, the peak frequency pxm has a larger difference value from a frequency spectrum in frequencies in the vicinity thereof. Further, the subject component removal means 41 determines, based on peak frequency pxm in the horizontal direction, a low frequency component to be removed.

As illustrated in FIG. 9, the subject component removal means 41 creates a band-pass filter having a passband of $fx_1 \leq f \leq fx_2$ including peak frequency pxm, and obtains subject component removed signal Sh by performing filtering processing on image signal Sd by the band-pass filter. In the passband characteristics, $fx_1$ and $fx_2$ may be set in an arbitrary manner as long as pxm is included. Here, predetermined value fc1 is added to or subtracted from pxm, and $fx_1$ and $fx_2$ are calculated as $fx_1 = pxm - fc1$ and $fx_2 = pxm + fc1$.

Then, the periodic pattern detection means 42 in the second embodiment detects a frequency component corresponding to a periodic pattern with respect to at least the other one of the first direction and the second direction (a different direction from a direction that has the clearer peak of a frequency spectrum of a frequency component corresponding to a periodic pattern) in a subject component removed signal. Here, the periodic pattern detection means 42 performs frequency analysis on subject component removed signal Sh with respect to the vertical direction, and detects, based on the obtained frequency spectrum, frequency component pym corresponding to a periodic pattern in the vertical direction.

Then, in a manner similar to the first embodiment, the suppression means 43 determines passband characteristics by using a known method in such a manner that the detected frequency components pxm and pym, which correspond to the periodic pattern, are included. Further, the suppression means 43 creates, based on the determined passband characteristics, band-stop filter BSF for each of a horizontal direction and a vertical direction. Then, the suppression means 43 extracts processed signal Sp, in which the periodic pattern has been suppressed, from image signal Sd by performing one-dimensional filtering processing using the band-stop filter BSF. Further, an image corresponding to the processed signal Sp is displayed on a display means, such as a monitor (not illustrated), or output to an output means, such as a printer (not illustrated).

According to the second embodiment, the subject component removal means 41 uses, as a subject component removal filter, a band-pass filter that extracts a spatial frequency component including a frequency component corresponding to a periodic pattern detected with respect to at least one of the first direction and the second direction from an image signal. Therefore, it is possible to set a more appropriate removal range for removing a subject component by performing subject component removal processing based on the detected frequency component corresponding to the periodic pattern. Further, it is possible to more appropriately remove the subject component. Hence, it is possible to accurately detect a frequency component corresponding to a periodic pattern, and to suppress error detection of the frequency component corresponding to the periodic pattern. According to the second embodiment, subject component removal processing is performed by a band-stop filter. Therefore, a remarkable effect of appropriate removal of a subject component is achievable.

According to the second embodiment, the subject component removal means 41 uses a subject component removal filter that removes, with respect to one of the first direction (horizontal direction) and the second direction (vertical direction) that has the clearer peak of a frequency spectrum of a frequency component corresponding to a periodic pattern, a lower spatial frequency component than the frequency component corresponding to the periodic pattern, and which has been detected with respect to the one of the first direction and the second direction, from image signal Sd. Therefore, processing for detecting, with respect to a direction in which it is difficult to clearly judge whether the frequency component corresponds to a periodic pattern, is performed based on a frequency component with respect to a direction in which it is possible to more clearly judge that the frequency component corresponds to the periodic pattern. Therefore, it is possible to accurately detect a frequency component corresponding to the periodic pattern. Hence, it is possible to appropriately suppress error detection of a frequency component corresponding to a periodic pattern.

In the second embodiment, the periodic pattern detection means 42 performs, with respect to a vertical direction, a frequency analysis on subject component removed signal Sh, and detects frequency component pym corresponding to a periodic pattern in the vertical direction based on the obtained frequency spectrum. Further, the periodic pattern detection means 42 may detect frequency component pxm again also in a horizontal direction. In such a case, it is possible to further improve the accuracy of detecting the frequency component corresponding to the frequency spectrum also in the horizontal direction.

The second embodiment may be applied also when a peak of a frequency spectrum is detected only in one of a vertical direction and a horizontal direction. First, subject component removal processing is performed with respect to the direction in which the peak has been detected based on the detected peak. After then, processing for detecting a periodic pattern in the subject component removed signal is performed with respect to the direction in which the peak has not been detected. Accordingly, it is possible to more appropriately apply the second embodiment. When a peak of a frequency spectrum has been detected only in one of the vertical direction and the horizontal direction, a user or an image processing apparatus may erroneously recognize that the periodic pattern is present only in one of the directions, and regard that the periodic pattern is not inclined. Further, the user or the image processing apparatus may perform erroneous periodic pattern suppression processing with respect to the direction in which no periodic pattern is recognized, or the like. Therefore, the periodic pattern is not appropriately suppressed, and there is a risk that the periodic pattern remains. However, when the second embodiment is applied to the direction in which the peak of the frequency spectrum has not been detected, it is possible to accurately detect the inclination of the periodic pattern. Further, it is possible to appropriately perform processing for suppressing the periodic pattern also with respect to the direction in which the frequency component corresponding to the periodic pattern has not been detected.

Further, in the second embodiment, the periodic pattern detection means 42 may perform subject component extraction processing only in one of the vertical direction and the horizontal direction. Further, subject component removal processing in the second embodiment may be performed by a high-pass filter.

In the second embodiment, the periodic pattern detection means 42 may determine subject component removal characteristics for respective directions based on both of the detected peaks pxm and pym. For example, a band-pass filter (or a high-pass filter) that passes a band including peak frequency pxm that has been detected with respect to the horizontal direction is created. Further, a band-pass filter (or a high-pass filter) that passes a band including peak frequency pym that has been detected with respect to the vertical direction is created. Further, filtering processing may be performed by each of the created filters. Since the subject component is removed more in both of the directions, it is possible to set a more appropriate removal range, and to more appropriately remove the subject component. Therefore, it is possible to more accurately detect a frequency component corresponding to a periodic pattern, and to suppress error detection of a frequency component corresponding to the periodic pattern.

The suppression means 43 may perform any suppression processing also in the second embodiment as long as processed signal Sp, in which a frequency component corresponding to a periodic pattern has been suppressed, is obtainable from image signal Sd. For example, band-pass filter BPF (or high-pass filter HPF) that passes a band including the detected frequency component corresponding to the periodic pattern may be created. Further, image signal Se extracted by the band-pass filter BPF (or high-pass filter HPF) may be subtracted from image signal Sd.

As a third embodiment, a warning means, which is not illustrated, may be provided. The warning means warns when frequency components corresponding a periodic pattern are detected in both of the first and second directions. Such a warning may be issued by using any method as long as the warning is identifiable by a user. For example, the warning may be issued by sound or by a visual means. As an example, warning display may be performed on a display screen. In such a case, it is possible to notify a user that the periodic pattern is inclined. Therefore, it is possible to reduce the risk of inappropriate periodic pattern suppression processing in which a user or an image processing apparatus erroneously recognizes that the periodic pattern is present only in one direction, and regards that the periodic pattern is not inclined, and performs erroneous periodic pattern suppression processing with respect to the direction in which the periodic pattern is not recognized, or the like. Hence, it is possible to appropriately suppress the periodic pattern.

In the embodiments of the present invention, a case in which the present invention is applied to a radiographic image readout apparatus (CR: Computed Radiography) has been described. In the radiographic image readout apparatus, excitation light, such as a laser beam, is output to a storable phosphor sheet, and stimulated emission light is generated. Photoelectric conversion is performed on the stimulated emission light to obtain an image signal. The present invention is not limited to the aforementioned embodiments, and may be applied to any type of radiographic image readout apparatus using a grid. For example, the present invention may be applied to a radiographic image readout apparatus using a radiation solid-state detector (hereinafter referred to as a radiation solid-state detector of "light conversion type and indirect conversion type"), and in which plural photoelectric conversion elements, each corresponding to a pixel, are two-dimensionally formed on an insulation substrate. A phosphor layer (scintillator) that converts radiation carrying image information into visible light by irradiation with the radiation is deposited and constitutes the radiation solid-state detector formed on the radiation image readout apparatus. Further, the present invention may be applied to a radiography apparatus using a radiation solid-state detector (hereinafter referred to as a radiation solid-state detector of "direct conversion type"). Plural charge collecting electrodes, each corresponding to a pixel, are two-dimensionally formed on an insulation substrate in a radiographic image readout apparatus. A radiation conductor that generates charges carrying image information by irradiation with radiation carrying the image information is deposited, and constitutes the radiation solid-state detector formed on the two-dimensional image readout apparatus.

Further, the present invention may be applied to a radiographic image readout apparatus using various kinds of radiation solid-state detector. As a radiation solid-state detector of light conversion type, radiation solid-state detectors disclosed, for example, in Japanese Unexamined Patent Publication No. 59(1984)-211263, Japanese Unexamined Patent publication No. 2(1990)-164067, U.S. Pat. No. 5,187,369, L. E. Antonuk et al., "Signal, noise, and readout considerations in the development of amorphous silicon photodiode arrays for radiotherapy and diagnostic x-ray imaging", Proc. SPIE, Vol. 1443, pp. 108-119, 1991, and the like may be adopted.

Meanwhile, as a radiation solid-state detector of direct conversion type, radiation solid-state detectors disclosed for example in (i) a radiation solid-state detector, the thickness of which in the transmission direction of radiation is set about ten times as thick as an ordinary one (S. Qureshi et al., "MATERIAL PARAMETERS IN THICK HYDROGENATED AMORPHOUS SILICON RADIATION DETECTORS", Journal of Non-Crystalline Solids, Vol. 114, Part 2, pp. 417-419, 1989), or (ii) a radiation solid-state detector, in which two or more layers are deposited in the transmission direction of radiation with a metal plate therebetween (Y. Naruse and T. Hatayama, "Metal/Amorphous Silicon Multilayer Radiation Detectors", Transactions on Nuclear Science, Vol. 36, No. 2, pp 1347-1352, 1989), or (iii) a radiation solid-state detector using CdTe or the like, disclosed in (Japanese Unexamined Patent Publication No. 1 (1989)-216290) or the like may be adopted.

Each of the aforementioned embodiments is only an example, and all of the descriptions should not be used to interpret the technical scope of the present invention in a limited manner. Further, the system configuration, the hardware configuration, the process flow, the module configuration, the specific content of processing and the like may be modified in various manners without departing from the gist of the present invention. Such modifications remain in the technical scope of the present invention.

What is claimed is:

1. An image processing apparatus that identifies an inclination of a periodic pattern included in an image based on spatial frequency components corresponding to the periodic pattern, and the spatial frequency components having been detected with respect to a plurality of directions, the apparatus comprising:
a subject component removal unit configured to obtain a subject component removed signal from an image signal representing the image by performing one-dimensional filtering processing using a subject component removal filter that removes low spatial frequency components including a subject component of the image, with respect to one of a first direction and a second direction that has a clearer peak among peaks of the spatial frequency spectra which are candidates of spatial frequencies corresponding to the periodic pattern in the first direction and the second direction, the second direction being different from the first direction; and
a periodic pattern detection unit configured to detect, with respect to both of the first direction and the second direction, the frequency components corresponding to the periodic pattern in the subject component removed signal,
wherein the subject component removal filter is a high-pass filter or a band-pass filter, which passes through the spatial frequency components corresponding to the clearer peak, with respect to the direction which has the clearer peak of the spatial frequency spectrum.

2. The image processing apparatus, as defined in claim 1, the apparatus further comprising:
a suppression unit configured to suppress the spatial frequency components corresponding to the periodic pattern in the image by performing one-dimensional filtering processing for suppressing the spatial frequency components corresponding to the periodic pattern with respect to both of the first direction and the second direction.

3. The image processing apparatus, as defined in claim 1, the apparatus further comprising:
a warning unit configured to warn when the spatial frequency components corresponding to the periodic pattern have been detected with respect to both of the first direction and the second direction.

4. The image processing apparatus, as defined in claim 1, wherein the periodic pattern detection unit detects the peaks which are candidates of spatial frequencies corresponding to the periodic pattern in the first direction and the second direction, by analyzing spatial frequencies spectra of the image signal.

5. The image processing apparatus, as defined in claim 1, wherein the periodic pattern detection unit calculates spatial frequency spectra of the image signal with respect to the first direction and the second direction, and detects as the two peaks of the frequency spectra which are candidates from the calculated spatial frequency spectra that has a largest difference in spatial frequencies in the vicinity thereof in each of the first direction and the second direction.

6. An image processing method that identifies an inclination of a periodic pattern included in an image based on spatial frequency components corresponding to the periodic pattern, and the spatial frequency components having been detected with respect to a plurality of directions, the method comprising the steps of:
obtaining a subject component removed signal from an image signal representing the image by performing one-dimensional filtering processing using a subject component removal filter that removes low spatial frequency components including a subject component of the image, with respect to one of a first direction and a second direction that has a clearer peak among peaks of the spatial frequency spectra which are candidates of spatial frequencies corresponding to the periodic pattern in the first direction and the second direction, the second direction being different from the first direction; and
detecting, with respect to both of the first direction and the second direction, the frequency components corresponding to the periodic pattern in the subject component removed signal,
wherein using a subject component removal filter is using a high-pass filter or a band-pass filter, which passes through the spatial frequency spectrum corresponding to the clearer peak, with respect to the direction which has the clearer peak of the spatial frequency spectrum.

7. A non-transitory computer-readable recording medium storing therein an image processing program that identifies an inclination of a periodic pattern included in an image based on spatial frequency components corresponding to the periodic pattern, and the spatial frequency components having been detected with respect to a plurality of directions, the program causing a computer to function as:

a subject component removal unit configured to obtain a subject component removed signal from an image signal representing the image by performing one-dimensional filtering processing using a subject component removal filter that removes low frequency components including a subject component of the image, with respect to one of a first direction and a second direction that has a clearer peak among peaks of the frequency spectra which are candidates of spatial frequencies corresponding to the periodic pattern in the first direction and the second direction, the second direction being different from the first direction; and a periodic pattern detection unit configured to detect, with respect to both of the first direction and the second direction, the frequency components corresponding to the periodic pattern in the subject component removed signal, wherein the subject component removal filter is a high-pass filter or a band-pass filter, which passes through the spatial frequency spectrum corresponding to the clearer peak, with respect to the direction which has the clearer peak of the spatial frequency spectrum.

8. An image processing apparatus that identifies an inclination of a periodic pattern included in an image based on spatial frequency components corresponding to the periodic pattern, and the spatial frequency components having been detected with respect to a plurality of directions, the apparatus comprising:

a periodic pattern detection unit configured to detect candidates of spatial frequencies corresponding to the periodic pattern from an image signal representing the image with respect to two different directions, and judges a first direction which has a clearer peak among peaks of the detected candidates of spatial frequencies corresponding to the periodic pattern with respect to the two different directions, and judges a first spatial frequency which has the clearer peak corresponding to the periodic pattern;

a subject component removal unit configured to obtain a subject component removed signal from the image signal representing the image by performing one-dimensional filtering processing using a subject component removal filter that pass through spatial frequencies including the judged first spatial frequency and removes a lower frequency component including a subject component of the image than the judged first spatial frequency with respect to the first direction; and the periodic pattern detection unit farther judges from the subject component removed signal a second spatial frequency corresponding to the periodic pattern in a second direction, the second direction being different from the first direction.

9. The image processing apparatus, as defined in claim 8, wherein the subject component removal filter is a high-pass filter or is a band-pass filter.

10. The image processing apparatus, as defined in claim 8, the apparatus further comprising:

a suppression unit configured to suppress the spatial frequency components corresponding to the periodic pattern in the image by performing one-dimensional filtering processing for suppressing the spatial frequency components corresponding to the periodic pattern, with respect to both of the first direction and the second direction.

11. The image processing apparatus, as defined in claim 8, the apparatus further comprising:

a warning unit configured to warn when the spatial frequency components corresponding to the periodic pattern have been detected with respect to both of the first direction and the second direction.

12. The image processing apparatus, as defined in claim 8, wherein the periodic pattern detection unit detects the peaks which are candidates of spatial frequencies corresponding to the periodic pattern in the first direction and the second direction, by analyzing spatial frequencies spectra of the image signal.

13. The image processing apparatus, as defined in claim 8, wherein the periodic pattern detection unit calculates spatial frequency spectra of the image signal with respect to the first direction and the second direction, and detects as the two peaks of the frequency spectra which are candidates from the calculated spatial frequency spectra that has a largest difference in spatial frequencies in the vicinity thereof in each of the first direction and the second direction.

* * * * *